US00PP23581P3

(12) United States Plant Patent
Sproul

(10) Patent No.: US PP23,581 P3
(45) Date of Patent: May 7, 2013

(54) SHRUB ROSE PLANT NAMED 'SPROLEMPINK'

(50) Latin Name: *Rosa hybrida*
Varietal Denomination: Sprolempink

(75) Inventor: James A. Sproul, Bakersfield, CA (US)

(73) Assignee: CP Delaware, Inc., Wilmington, DE (US)

( * ) Notice: Subject to any disclaimer, the term of this patent is extended or adjusted under 35 U.S.C. 154(b) by 22 days.

(21) Appl. No.: 13/067,813

(22) Filed: Jun. 28, 2011

(65) Prior Publication Data

US 2013/0007931 P1 Jan. 3, 2013

(51) Int. Cl.
*A01H 5/00* (2006.01)

(52) U.S. Cl. ..... Plt./107; Plt./101; Plt./102

(58) Field of Classification Search ..... Plt./101, Plt./102, 107
See application file for complete search history.

*Primary Examiner* — Susan McCormick Ewoldt

(74) *Attorney, Agent, or Firm* — Buchanan Ingersoll & Rooney

(57) ABSTRACT

A new and distinct variety of shrub rose plant is provided which forms in abundance on a substantially continuous basis attractive semi-double pink blossoms having a blotch of burgundy coloration at the center. The vegetation is strong and the growth habit is compact and bushy. Attractive ornamental glossy dark green foliage is formed. Above average resistance to blackspot for the type is exhibited. Additionally, the new variety is particularly well suited for growing as distinctive ornamentation in the landscape.

1 Drawing Sheet

Botanical/commercial classification: *Rosa hybrida*/Shrub Rose Plant.

Varietal denomination: cv. Sprolempink.

SUMMARY OF THE INVENTION

The new variety of shrub rose plant of the present invention was created by artificial pollination carried out during 2007 at Bakersfield, Calif., U.S.A., wherein two parents were crossed which previously had been studied in the hope that they would contribute the desired characteristics. The female parent (i.e., the seed parent) was an unnamed rose seedling (non-patented in the United States). The male parent (i.e., the pollen parent) of the new variety was supplied by the use of mixed *Hulthemia persicas* pollen (non-patented in the United States). The parentage of the present invention can be summarized as follows:

Unnamed Seedling×Mixed *Hulthemia persicas* Pollen.

The seeds resulting from the above pollination were sown during 2008 and small plants were obtained which were physically and biologically different from each other. Selective study resulted in the identification of a single plant of the new variety.

It was found that the new variety of shrub rose plant of the present invention possesses the following combination of characteristics:

(a) abundantly and substantially continuously forms attractive semi-double pink blossoms having a blotch of burgundy coloration at the center,
(b) exhibits a compact and bushy growth habit,
(c) forms attractive ornamental dark green foliage with a glossy finish, and
(d) exhibits above average resistance to blackspot for the type.

A new rose variety is provided having attractive semi-double pink and burgundy blooms, combined with substantially continuous blooming and above average resistance to blackspot for the type.

The new variety well meets the needs of the horticultural industry. It can be grown to advantage as attractive ornamentation in parks, gardens, public areas, and residential landscapes. The new variety is particularly well suited for growing in the Western U.S.A. landscape. The pink and burgundy blossoms contrast nicely with the dark green foliage.

The characteristics of the new variety have been found to be homogeneous and stable and are strictly transmissible by asexual propagation at Wasco, Calif., U.S.A., such as budding, grafting, and vegetative propagation from one generation to another. Accordingly, the new variety can be asexually reproduced in a true-to-type manner.

The new variety has been named 'Sprolempink' and will be marketed under the EYECONIC PINK LEMONADE trademark.

The new variety can be readily distinguished from other *Hulthemia persicas* rose plants. Such *Hulthemia* rose plants generally bloom only once a year, are susceptible to diseases such as blackspot, and generally display an unattractive growth habit. It is found that the new variety will maintains on the blossoms a central burgundy blotch that is a defining mark of *Hulthemias*, and combines this with a reblooming character, increased resistance to blackspot, and an attractive compact and bushy growth habit. Accordingly, the new variety is demonstrated to display the improved qualities of reblooming, disease resistance, and attractive growth habit, unlike those commonly displayed by other *Hulthemia* hybrids to date.

BRIEF DESCRIPTION OF THE PHOTOGRAPH

The accompanying photograph shows, as nearly true as it is reasonably possible to make the same in a color illustration of this character, typical blossoms of the new variety.

The illustrated plant was approximately two years of age and was being grown during June on its own roots outdoors in the field at Wasco, Calif., U.S.A.

DETAILED DESCRIPTION

The chart used in the identification of colors is that of The Royal Horticultural Society (R.H.S. Colour Chart). The description is based on the observation of two-year-old specimens except as otherwise indicated of the new variety during June while grown outdoors on their own roots at West Grove, Pa., U.S.A.

Class: Shrub Rose.

Plant:

*Height*.—Approximately 3 feet on average at the end of the growing season.

*Width*.—Approximately 3 feet on average at the end of the growing season.

*Habit*.—Compact, and bushy.

Branches:

*Color*. —Young stems: near Yellow-Green Group 144A.

*Number*.—Commonly approximately 9 on average for a three-year-old plant.

*Length*.—Commonly approximately 25 cm on average for a three-year-old plant.

*Diameter*.—Commonly approximately 9 mm on average for a three-year-old plant.

*Thorns*.—Size: approximately 5 mm in length and approximately 1 to 2 mm in diameter on average at the base. Color. Greyed-Orange Group 171C.

Leaves:

*Leaflets number:* 3, 5, and 7. Shape: ovate with a serrulate margin, rounded base, and acuminate tip. Size: terminal leaflets commonly are approximately 3.5 cm in length and approximately 3.5 cm in width on average, and lower leaflets commonly are approximately 2 cm in length and approximately 1.3 cm in width on average. Texture: smooth on the upper surface and mostly smooth on the under surface commonly with some roughness around the midrib. Overall appearance: very dense, leathery, and dark green in coloration, with a glossy finish. Color (adult foliage): upper surface: commonly near Yellow Green Group 138A. under surface: commonly near Green Group 138B. leaflet margins: Greyed-Red Group 182A. Venation pattern: net-veined. Vein color: near Green Group 143C.

*Stipules*.—Length: commonly approximately 1 cm on average. Width: commonly approximately 1 mm on average.

*Rachis*.—Length: commonly approximately 3 cm on average. Diameter: commonly approximately 1 mm on average.

Inflorescence:

*Number of flowers*.—Commonly approximately 5 blooms per stem on average in a cluster.

*Peduncle*.—Yellow-Green Group 144B, approximately 4 cm in length on average and approximately 2 to 3 mm in diameter on average.

*Sepals*.—Number: five. Size: commonly approximately 2 cm in length and approximately 9 mm in width at the widest point on average. Upper surface: near Yellow-Green Group 145C, somewhat soft, and moderately tomentose. Under surface: near Yellow-Green Group 144B, smooth in texture, and mildly hispidulous.

*Buds*.—Shape: ovoid. Length: approximately 2 cm on average. Diameter: commonly approximately 1.5 cm on average. Color: near Red Group 50A when opening.

*Flower*.—Form: cuplike and semi-double. Diameter: approximately 7 cm on average. Color: upper surface: generally pink with a burgundy central blotch, outer portions of the petals are near Red Group 38D, transitioning to a narrow portion of near Yellow Group 4C, and subsequently transitioning to near Red Group 45D to form a dark burgundy central blotch approaching the point of attachment. under surface: Red Group 36A toward the apex and Yellow Group 3D at the point of attachment. Fragrance: none noticeable. Petal number: approximately 10 on average. Petal length: commonly approximately 3 cm on average. Petal width: commonly approximately 3.3 cm on average at the widest point. Petal margin: entire. Petal texture: glabrous on both surfaces. Petal apex: broadly obcordate. Petal base: broadly cuneate. Petaloids: none observed during observations to date. Petal drop: good, with the petals commonly dropping cleanly and freely. Stamen number: approximately 80 to 90 on average. Anthers: Yellow-Orange Group 22A in coloration. Filaments: commonly near Yellow Group 6A on the upper two-thirds, Red Group 43A on the lower two-thirds, and commonly approximately 5 to 10 mm in length. Pistils: separate and free, and commonly approximately 30 to 40 in number on average. Receptacle: achenes stand on the bottom and wall.

Development:

*Vegetation*.—Strong.

*Blossoming*.—Abundant and substantially continuous.

*Resistance to diseases*.—Above average for the type with respect to blackspot, mildew, and rust.

*Propensity to form hips/seeds*.—Sparse.

*Hardiness*.—U.S.D.A. Hardiness Zone Nos. 6 to 9.

Plants of the new 'Sprolempink' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of shrub rose plant characterized by the following combination of characteristics:

(a) abundantly and substantially continuously forms attractive semi-double pink blossoms having a blotch of burgundy coloration at the center, (b) exhibits a compact and bushy growth habit, (c) forms attractive ornamental dark green foliage with a glossy finish, and (d) exhibits above average resistance to blackspot for the type;

substantially as herein shown and described.

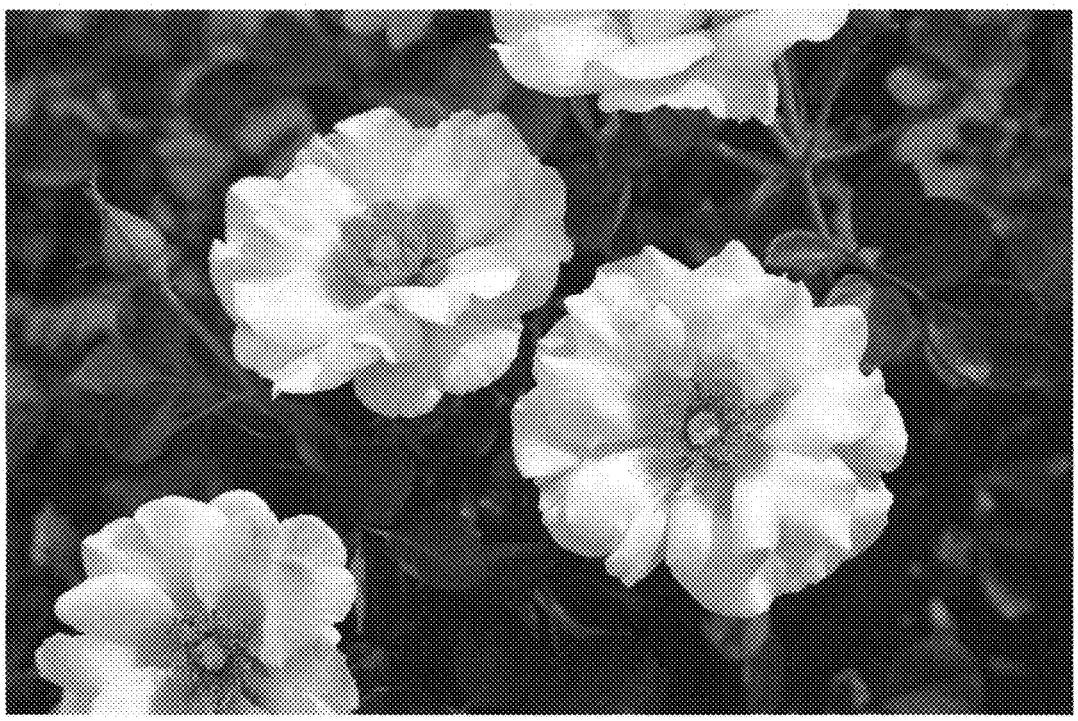

* * * * *